(12) United States Patent
Lands et al.

(10) Patent No.: US 7,887,535 B2
(45) Date of Patent: Feb. 15, 2011

(54) VESSEL SEALING WAVE JAW

(75) Inventors: Michael J. Lands, Louisville, CO (US);
Stephen Wade Lukianow, Nederland, CO (US); Steven P. Buysse, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1281 days.

(21) Appl. No.: 10/919,615

(22) Filed: Aug. 17, 2004

(65) Prior Publication Data
US 2005/0101952 A1    May 12, 2005

Related U.S. Application Data

(63) Continuation of application No. 09/419,592, filed on Oct. 18, 1999, now Pat. No. 6,887,240.

(51) Int. Cl.
*A61B 17/28* (2006.01)
*A61B 18/12* (2006.01)

(52) U.S. Cl. ........................................ 606/51
(58) Field of Classification Search ............. 606/50–52, 606/205; D24/143
See application file for complete search history.

(56) References Cited

U.S. PATENT DOCUMENTS

| | | | |
|---|---|---|---|
| 371,664 A | 10/1887 | Brannan et al. | |
| 702,472 A | 6/1902 | Pignolet | |
| 728,883 A | 5/1903 | Downes | |
| 1,586,645 A | 6/1926 | Bierman | |
| 1,813,902 A | 7/1931 | Bovie | |
| 2,002,594 A | 5/1935 | Wappler et al. | |
| 2,011,169 A | 8/1935 | Wappler | |
| 2,031,682 A | 2/1936 | Wappler et al. | |

(Continued)

FOREIGN PATENT DOCUMENTS

CA    2104423    2/1994

(Continued)

OTHER PUBLICATIONS

"Innovations in Electrosurgery" Sales/Product Literature; Dec. 31, 2000.

(Continued)

*Primary Examiner*—Eduardo C Robert
*Assistant Examiner*—David Comstock

(57) ABSTRACT

A forceps for clamping, grasping, manipulating, coagulating/desiccating and cutting tissue includes a shaft portion having a proximal end, a distal end and first and second jaw members pivotally attached to the distal end of the shaft by a pivot assembly. Each of the jaw members including an opposing inner facing surface having a plurality of wave forms disposed thereon for engaging tissue therebetween. The wave forms disposed on the inner facing surface of the second jaw member being complimentary to the wave forms on the inner facing surface of first jaw member. A handle portion having an actuating assembly is attached to the proximal end of the shaft for imparting movement of the first and second jaw members from a first open position wherein the jaw members are disposed in spaced relation relative to one another to a second clamping position wherein the jaw members cooperate to grasp tissue therebetween. One embodiment of the forceps includes a pair of electrodes clamped on the inner facing surface of each jaw member for imparting electrosurgical energy to the tissue grasped therebetween.

30 Claims, 9 Drawing Sheets

U.S. PATENT DOCUMENTS

| | | |
|---|---|---|
| 2,176,479 A | 10/1939 | Willis |
| 2,305,156 A | 4/1941 | Grubel |
| 2,279,753 A | 4/1942 | Knopp |
| 2,632,661 A | 8/1948 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,720,896 A | 3/1973 | Beierlein |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | Digeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |

| | | | | | | |
|---|---|---|---|---|---|---|
| 5,509,922 A | 4/1996 | Aranyi et al. | | 5,797,941 A | 8/1998 | Schulze et al. |
| 5,514,134 A | 5/1996 | Rydell et al. | | 5,797,958 A | 8/1998 | Yoon |
| 5,527,313 A | 6/1996 | Scott et al. | | 5,800,449 A | 9/1998 | Wales |
| 5,531,744 A | 7/1996 | Nardella et al. | | 5,807,393 A | 9/1998 | Williamson, IV et al. |
| 5,536,251 A | 7/1996 | Evard et al. | | 5,810,808 A | 9/1998 | Eggers |
| 5,540,684 A | 7/1996 | Hassler, Jr. | | 5,810,811 A | 9/1998 | Yates et al. |
| 5,540,685 A | 7/1996 | Parins et al. | | 5,810,877 A | 9/1998 | Roth et al. |
| 5,540,715 A | 7/1996 | Katsaros et al. | | 5,814,043 A | 9/1998 | Shapeton |
| 5,542,945 A | 8/1996 | Fritzsch | | 5,817,093 A | 10/1998 | Williamson, IV et al. |
| 5,558,671 A | 9/1996 | Yates | | 5,820,630 A | 10/1998 | Lind |
| 5,558,672 A | 9/1996 | Edwards et al. | | 5,827,271 A | 10/1998 | Buysse et al. |
| 5,562,699 A | 10/1996 | Heimberger et al. | | 5,827,279 A | 10/1998 | Hughett et al. |
| 5,569,241 A | 10/1996 | Edwardds | | 5,827,281 A | 10/1998 | Levin |
| 5,569,243 A | 10/1996 | Kortenbach et al. | | 5,827,323 A | 10/1998 | Klieman et al. |
| 5,571,100 A | 11/1996 | Goble et al. | | 5,827,548 A | 10/1998 | Lavallee et al. |
| 5,573,424 A | 11/1996 | Poppe | | 5,833,690 A | 11/1998 | Yates et al. |
| 5,573,534 A | 11/1996 | Stone | | 5,843,080 A | 12/1998 | Fleenor et al. |
| 5,573,535 A | 11/1996 | Viklund | | 5,849,022 A | 12/1998 | Sakashita et al. |
| 5,575,805 A | 11/1996 | Li | | 5,853,412 A | 12/1998 | Mayenberger |
| 5,578,052 A | 11/1996 | Koros et al. | | 5,860,976 A | 1/1999 | Billings et al. |
| 5,582,611 A | 12/1996 | Tsukagoshi et al. | | 5,876,401 A | 3/1999 | Schulze et al. |
| 5,585,896 A | 12/1996 | Yamazaki et al. | | 5,882,567 A | 3/1999 | Cavallaro et al. |
| 5,590,570 A | 1/1997 | LeMaire, III et al. | | 5,891,141 A | 4/1999 | Rydell |
| 5,601,601 A | 2/1997 | Tal et al. | | 5,891,142 A | 4/1999 | Eggers et al. |
| 5,603,711 A | 2/1997 | Parins et al. | | 5,893,863 A | 4/1999 | Yoon |
| 5,603,723 A | 2/1997 | Aranyi et al. | | 5,893,875 A | 4/1999 | O'Connor et al. |
| 5,611,798 A | 3/1997 | Eggers | | 5,893,877 A | 4/1999 | Gampp, Jr. et al. |
| 5,620,453 A | 4/1997 | Nallakrishnan | | 5,902,301 A | 5/1999 | Olig |
| 5,624,452 A | 4/1997 | Yates | | 5,906,630 A | 5/1999 | Anderhub et al. |
| 5,626,578 A | 5/1997 | Tihon | | 5,908,420 A | 6/1999 | Parins et al. |
| 5,626,609 A | 5/1997 | Zvenyatsky et al. | | 5,908,432 A | 6/1999 | Pan |
| 5,630,833 A | 5/1997 | Katsaros et al. | | 5,911,719 A | 6/1999 | Eggers |
| 5,637,110 A | 6/1997 | Pennybacker et al. | | 5,913,874 A | 6/1999 | Berns et al. |
| 5,638,003 A | 6/1997 | Hall | | 5,921,984 A | 7/1999 | Sutcu et al. |
| 5,643,294 A | 7/1997 | Tovey et al. | | 5,925,043 A | 7/1999 | Kumar et al. |
| 5,647,869 A | 7/1997 | Goble et al. | | 5,935,126 A | 8/1999 | Riza |
| 5,647,871 A | 7/1997 | Levine et al. | | 5,944,718 A | 8/1999 | Dafforn et al. |
| 5,649,959 A | 7/1997 | Hannam et al. | | 5,951,549 A | 9/1999 | Richardson et al. |
| 5,658,281 A | 8/1997 | Heard | | 5,954,720 A | 9/1999 | Wilson et al. |
| 5,662,667 A | 9/1997 | Knodel | | 5,957,923 A | 9/1999 | Hahnen et al. |
| 5,665,100 A | 9/1997 | Yoon | | 5,960,544 A | 10/1999 | Beyers |
| 5,667,526 A | 9/1997 | Levin | | 5,961,514 A | 10/1999 | Long et al. |
| 5,674,220 A | 10/1997 | Fox et al. | | 5,964,758 A | 10/1999 | Dresden |
| 5,681,282 A | 10/1997 | Eggers et al. | | 5,976,132 A | 11/1999 | Morris |
| 5,688,270 A | 11/1997 | Yates et al. | | 5,984,939 A | 11/1999 | Yoon |
| 5,693,051 A | 12/1997 | Schulze et al. | | 5,989,277 A | 11/1999 | LeMaire, III et al. |
| 5,695,522 A | 12/1997 | LeMaire, III et al. | | 5,997,565 A | 12/1999 | Inoue |
| 5,700,261 A | 12/1997 | Brinkerhoff | | 6,004,335 A | 12/1999 | Vaitekunas et al. |
| 5,702,390 A | 12/1997 | Austin et al. | | 6,010,516 A | 1/2000 | Hulka et al. |
| 5,707,369 A | 1/1998 | Vaitekunas et al. | | 6,024,741 A | 2/2000 | Williamson et al. |
| 5,709,680 A | 1/1998 | Yates et al. | | 6,024,744 A | 2/2000 | Kese et al. |
| 5,716,366 A | 2/1998 | Yates | | 6,030,384 A | 2/2000 | Nezhat |
| 5,720,744 A | 2/1998 | Eggleston et al. | | 6,033,399 A | 3/2000 | Gines |
| 5,722,421 A | 3/1998 | Francese et al. | | 6,039,733 A | 3/2000 | Buysse et al. |
| 5,725,536 A | 3/1998 | Oberlin et al. | | 6,041,679 A | 3/2000 | Slater et al. |
| 5,727,428 A | 3/1998 | LeMaire, III et al. | | 6,050,996 A | 4/2000 | Schmaltz et al. |
| 5,735,848 A | 4/1998 | Yates et al. | | 6,053,914 A | 4/2000 | Eggers et al. |
| 5,743,906 A | 4/1998 | Parins et al. | | 6,053,933 A | 4/2000 | Balazs et al. |
| 5,755,717 A | 5/1998 | Yates et al. | | D424,694 S | 5/2000 | Tetzlaff et al. |
| 5,766,130 A | 6/1998 | Selmonosky | | D425,201 S | 5/2000 | Tetzlaff et al. |
| 5,766,166 A | 6/1998 | Hooven | | 6,059,782 A | 5/2000 | Novak et al. |
| 5,766,170 A | 6/1998 | Eggers | | 6,074,386 A | 6/2000 | Goble et al. |
| 5,769,849 A | 6/1998 | Eggers | | RE36,795 E | 7/2000 | Rydell |
| 5,772,655 A | 6/1998 | Bauer et al. | | 6,083,223 A | 7/2000 | Baker |
| 5,772,670 A | 6/1998 | Brosa | | 6,086,586 A | 7/2000 | Hooven |
| 5,776,128 A | 7/1998 | Eggers | | 6,090,107 A | 7/2000 | Borgmeier et al. |
| 5,776,130 A | 7/1998 | Buysse et al. | | 6,096,037 A | 8/2000 | Mulier et al. |
| 5,779,701 A | 7/1998 | McBrayer et al. | | 6,099,550 A | 8/2000 | Yoon |
| H1745 H | 8/1998 | Paraschac | | 6,102,909 A | 8/2000 | Chen et al. |
| 5,792,137 A | 8/1998 | Carr et al. | | 6,110,171 A | 8/2000 | Rydell |
| 5,792,177 A | 8/1998 | Kaseda | | 6,113,596 A | 9/2000 | Hooven et al. |
| 5,797,927 A | 8/1998 | Yoon | | 6,113,598 A | 9/2000 | Baker |
| 5,797,938 A | 8/1998 | Paraschac et al. | | 6,117,158 A | 9/2000 | Measamer et al. |

| | | | | | | |
|---|---|---|---|---|---|---|
| 6,123,701 | A | 9/2000 | Nezhat | 6,676,660 B2 | 1/2004 | Wampler et al. |
| H1904 | H | 10/2000 | Yates et al. | 6,679,882 B1 | 1/2004 | Kornerup |
| 6,126,658 | A | 10/2000 | Baker | 6,682,528 B2 | 1/2004 | Frazier et al. |
| 6,152,923 | A | 11/2000 | Ryan | 6,685,724 B1 | 2/2004 | Haluck |
| 6,162,220 | A | 12/2000 | Nezhat | 6,689,131 B2 | 2/2004 | McClurken |
| 6,174,309 | B1 | 1/2001 | Wrublewski et al. | 6,692,445 B2 | 2/2004 | Roberts et al. |
| 6,179,834 | B1 | 1/2001 | Buysse et al. | 6,695,840 B2 | 2/2004 | Schulze |
| 6,179,837 | B1 | 1/2001 | Hooven | 6,702,810 B2 | 3/2004 | McClurken et al. |
| 6,183,467 | B1 | 2/2001 | Shapeton et al. | 6,726,068 B2 | 4/2004 | Miller |
| 6,187,003 | B1 | 2/2001 | Buysse et al. | 6,726,686 B2 | 4/2004 | Buysse et al. |
| 6,190,386 | B1 | 2/2001 | Rydell | 6,733,498 B2 | 5/2004 | Paton et al. |
| 6,193,718 | B1 | 2/2001 | Kortenbach et al. | 6,736,813 B2 | 5/2004 | Yamauchi et al. |
| 6,206,876 | B1 | 3/2001 | Levine et al. | 6,743,229 B2 | 6/2004 | Buysse et al. |
| 6,206,877 | B1 | 3/2001 | Kese et al. | 6,743,230 B2 | 6/2004 | Lutze et al. |
| 6,217,602 | B1 | 4/2001 | Redmon | 6,757,977 B2 | 7/2004 | Dambal et al. |
| 6,221,039 | B1 | 4/2001 | Durgin et al. | 6,770,072 B1 | 8/2004 | Truckai et al. |
| 6,224,593 | B1 | 5/2001 | Ryan et al. | 6,773,409 B2 | 8/2004 | Truckai et al. |
| 6,228,080 | B1 | 5/2001 | Gines | 6,773,434 B2 | 8/2004 | Ciarrocca |
| 6,228,083 | B1 | 5/2001 | Lands et al. | 6,775,575 B2 | 8/2004 | Bommannan et al. |
| 6,267,761 | B1 | 7/2001 | Ryan | 6,776,780 B2 | 8/2004 | Mulier et al. |
| 6,270,497 | B1 | 8/2001 | Sekino et al. | 6,790,217 B2 | 9/2004 | Schulze et al. |
| 6,270,508 | B1 | 8/2001 | Klieman et al. | 6,796,981 B2 | 9/2004 | Wham et al. |
| 6,273,887 | B1 | 8/2001 | Yamauchi et al. | D496,997 S | 10/2004 | Dycus et al. |
| 6,277,117 | B1 | 8/2001 | Tetzlaff et al. | 6,802,843 B2 | 10/2004 | Truckai et al. |
| 6,280,458 | B1 | 8/2001 | Boche et al. | 6,808,525 B2 | 10/2004 | Latterell et al. |
| 6,283,961 | B1 | 9/2001 | Underwood et al. | D499,181 S | 11/2004 | Dycus et al. |
| D449,886 | S | 10/2001 | Tetzlaff et al. | 6,818,000 B2 | 11/2004 | Muller et al. |
| 6,302,424 | B1 | 10/2001 | Gisinger et al. | 6,887,240 B1 | 5/2005 | Lands et al. |
| 6,319,451 | B1 | 11/2001 | Brune | 6,926,716 B2 | 8/2005 | Baker et al. |
| 6,322,561 | B1 | 11/2001 | Eggers et al. | 6,929,644 B2 | 8/2005 | Truckai et al. |
| 6,334,860 | B1 | 1/2002 | Dorn | 6,932,810 B2 | 8/2005 | Ryan |
| 6,334,861 | B1 | 1/2002 | Chandler et al. | 6,932,816 B2 | 8/2005 | Phan |
| 6,345,532 | B1 | 2/2002 | Coudray et al. | 6,934,134 B2 | 8/2005 | Mori et al. |
| 6,350,264 | B1 | 2/2002 | Hooven | 6,936,061 B2 | 8/2005 | Sasaki |
| 6,352,536 | B1 | 3/2002 | Buysse et al. | 6,942,662 B2 | 9/2005 | Goble et al. |
| 6,358,249 | B1 | 3/2002 | Chen et al. | 6,953,461 B2 | 10/2005 | McClurken et al. |
| 6,358,268 | B1 | 3/2002 | Hunt et al. | 6,958,070 B2 | 10/2005 | Witt et al. |
| D457,958 | S | 5/2002 | Dycus et al. | 6,960,210 B2 | 11/2005 | Lands et al. |
| D457,959 | S | 5/2002 | Tetzlaff et al. | 6,964,662 B2 | 11/2005 | Kidooka |
| 6,387,094 | B1 | 5/2002 | Eitenmuller | 6,966,907 B2 | 11/2005 | Goble |
| 6,391,035 | B1 | 5/2002 | Appleby et al. | 6,977,495 B2 | 12/2005 | Donofrio |
| 6,398,779 | B1 | 6/2002 | Buysse et al. | 6,979,786 B2 | 12/2005 | Aukland et al. |
| 6,402,747 | B1 | 6/2002 | Lindemann et al. | 6,994,707 B2 | 2/2006 | Ellman et al. |
| 6,409,728 | B1 | 6/2002 | Ehr et al. | 6,994,709 B2 | 2/2006 | Iida |
| H2037 | H | 7/2002 | Yates et al. | 7,011,657 B2 | 3/2006 | Truckai et al. |
| 6,419,675 | B1 | 7/2002 | Gallo, Sr. | 7,033,354 B2 | 4/2006 | Keppel |
| 6,425,896 | B1 | 7/2002 | Baltschun et al. | 7,033,356 B2 | 4/2006 | Latterell et al. |
| 6,440,144 | B1 | 8/2002 | Bacher | 7,041,102 B2 | 5/2006 | Truckai et al. |
| 6,443,952 | B1 | 9/2002 | Mulier et al. | 7,044,948 B2 | 5/2006 | Keppel |
| 6,443,970 | B1 | 9/2002 | Schulze et al. | 7,052,496 B2 | 5/2006 | Yamauchi |
| 6,451,018 | B1 | 9/2002 | Lands et al. | D525,361 S | 7/2006 | Hushka |
| 6,458,125 | B1 | 10/2002 | Cosmescu | 7,070,597 B2 | 7/2006 | Truckai et al. |
| 6,458,128 | B1 | 10/2002 | Schulze | 7,083,618 B2 | 8/2006 | Couture et al. |
| 6,458,130 | B1 | 10/2002 | Frazier et al. | 7,083,619 B2 | 8/2006 | Truckai et al. |
| 6,464,701 | B1 | 10/2002 | Hooven et al. | 7,087,054 B2 | 8/2006 | Truckai et al. |
| 6,464,702 | B2 | 10/2002 | Schulze et al. | 7,090,673 B2 | 8/2006 | Dycus et al. |
| 6,464,704 | B2 | 10/2002 | Schmaltz et al. | 7,090,689 B2 | 8/2006 | Nagase et al. |
| 6,500,176 | B1 | 12/2002 | Truckai et al. | 7,101,371 B2 | 9/2006 | Dycus et al. |
| 6,511,480 | B1 | 1/2003 | Tetzlaff et al. | 7,101,372 B2 | 9/2006 | Dycus et al. |
| 6,514,252 | B2 | 2/2003 | Nezhat et al. | 7,101,373 B2 | 9/2006 | Dycus et al. |
| 6,527,771 | B1 | 3/2003 | Weadock et al. | 7,103,947 B2 | 9/2006 | Sartor et al. |
| 6,558,385 | B1 | 5/2003 | McClurken et al. | 7,112,199 B2 | 9/2006 | Cosmescu |
| 6,562,037 | B2 | 5/2003 | Paton et al. | D531,311 S | 10/2006 | Guerra et al. |
| 6,585,735 | B1 | 7/2003 | Frazier et al. | 7,115,123 B2 | 10/2006 | Knowlton et al. |
| 6,616,658 | B2 | 9/2003 | Ineson | 7,118,570 B2 | 10/2006 | Tetzlaff et al. |
| 6,616,661 | B2 | 9/2003 | Wellman et al. | 7,118,587 B2 | 10/2006 | Dycus et al. |
| 6,620,161 | B2 | 9/2003 | Schulze et al. | 7,131,860 B2 | 11/2006 | Sartor et al. |
| 6,626,901 | B1 | 9/2003 | Treat et al. | 7,131,970 B2 | 11/2006 | Moses et al. |
| 6,641,595 | B1 | 11/2003 | Moran et al. | 7,131,971 B2 | 11/2006 | Dycus et al. |
| 6,652,514 | B2 | 11/2003 | Ellman et al. | 7,135,020 B2 | 11/2006 | Lawes et al. |
| 6,652,521 | B2 | 11/2003 | Schulze | D533,942 S | 12/2006 | Kerr et al. |
| 6,656,177 | B2 | 12/2003 | Truckai et al. | 7,145,757 B2 | 12/2006 | Shea et al. |
| 6,669,696 | B2 | 12/2003 | Bacher et al. | 7,147,638 B2 | 12/2006 | Chapman et al. |

| | | |
|---|---|---|
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0176762 A1 | 9/2004 | Lawes et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |

| Pub. No. | Date | Name |
|---|---|---|
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0045947 A1 | 2/2008 | Johnson et al. |
| 2008/0058802 A1 | 3/2008 | Couture et al. |
| 2008/0082100 A1 | 4/2008 | Orton et al. |

FOREIGN PATENT DOCUMENTS

| | | |
|---|---|---|
| DE | 2415263 | 10/1975 |
| DE | 2627679 | 1/1977 |
| DE | 8712328 | 3/1988 |
| DE | 4303882 | 8/1994 |
| DE | 29616210 | 1/1997 |
| DE | 19608716 | 4/1997 |
| DE | 19751106 | 5/1998 |
| DE | 19751108 | 5/1999 |
| EP | 0364216 A1 | 4/1990 |
| EP | 0518230 A1 | 12/1992 |
| EP | 0 541 930 B1 | 5/1993 |
| EP | 0572131 | 12/1993 |
| EP | 0589453 A2 | 3/1994 |
| EP | 0584787 A1 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1645238 A1 | 4/2006 |
| EP | 1645240 A2 | 4/2006 |
| EP | 1707143 A1 | 10/2006 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 10/1971 |
| SU | 401367 | 11/1974 |
| WO | WO89/00757 | 1/1989 |
| WO | WO 92/04873 | 4/1992 |
| WO | WO 92/06642 | 4/1992 |
| WO | WO 94/08524 A | 4/1994 |
| WO | WO94/20025 | 9/1994 |
| WO | WO 95/02369 | 1/1995 |
| WO | WO95/07662 | 3/1995 |
| WO | WO 95/07662 | 3/1995 |
| WO | WO95/15124 | 6/1995 |
| WO | WO96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 A | 3/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 99/66850 A | 12/1999 |
| WO | WO 00/24330 | 5/2000 |
| WO | WO 00/24331 | 5/2000 |
| WO | WO00/24331 | 5/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO02/07627 | 1/2002 |
| WO | WO 02/067798 A1 | 9/2002 |
| WO | WO02/080783 | 10/2002 |
| WO | WO 02/080783 | 10/2002 |
| WO | WO02/080784 | 10/2002 |
| WO | WO 02/080784 | 10/2002 |
| WO | WO 02/080785 | 10/2002 |
| WO | WO02/080785 | 10/2002 |
| WO | WO 02/080786 | 10/2002 |
| WO | WO02/080786 | 10/2002 |
| WO | WO02/080793 | 10/2002 |
| WO | WO 02/080793 | 10/2002 |

| | | |
|---|---|---|
| WO | WO 02/080794 | 10/2002 |
| WO | WO02/080794 | 10/2002 |
| WO | WO 02/080795 | 10/2002 |
| WO | WO 02/080796 | 10/2002 |
| WO | WO 02/080796 A1 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO02/081170 | 10/2002 |
| WO | WO 02/081170 | 10/2002 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 A1 | 6/2004 |
| WO | WO 2004/073488 A2 | 9/2004 |
| WO | WO2004/073490 | 9/2004 |
| WO | WO 2004/073490 | 9/2004 |
| WO | WO2004/073753 | 9/2004 |
| WO | WO 2004/082495 | 9/2004 |
| WO | WO 2004/082495 A1 | 9/2004 |
| WO | WO 2004/098383 A1 | 11/2004 |
| WO | WO 2004/103156 | 12/2004 |
| WO | 2005/004734 A1 | 1/2005 |
| WO | WO2005/004735 | 1/2005 |
| WO | WO 2005/110264 | 11/2005 |

OTHER PUBLICATIONS

LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessal Sealing Device Hemorrhoidectomy" Sales Product Literature; Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature.
LigaSure Vessel Sealing System, the Seal of Confidence in General, Gynecologic, Urologic, and Laparaoscopic Surgery Sales/Product Literature.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC.
"Reducing Needlestick Injuries in the Operating Room" Sales/Product Literature.
Chung et al., "Clinical Experience of Sutureless Closed Hemorrhoidectomy with LigaSure" Diseases of the Colon & Rectum vol. 46, No. 1 Jan. 2003.
Strasberg et al., "Use of the Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature.
Michael Choti, "Abdominoperineal Resection with the LigaSure Vessel Sealing System and LigaSure Atlas 20 cm Open Instrument" Innovations that work, Jun. 2003.

Craig Johnson, "Use of the LigaSure Vessel Sealing System in Bloodless Hemorrhoidectomy" Innovations that Work, Mar. 2000.

Muller et al., "Extended Left Hemicolectomy Using the LigaSure Vessel Sealing System" Innovations that Work, Sep. 1999.

Herman et al., "Laparoscopic Intestinal Resection with the LigaSure Vessel Sealing System: A Case Report" Innovations that Work, Feb. 2002.

Carus et al., "Initial Experience with the LigaSure Vessel Sealing System in Abdominal Surgery" Innovations that Work, Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing for Hemostasis During Gynecologic Surgery" Sales/Product Literature.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al. "Radical Cystectomy in Females" Current Surgical Techniques in Urology, vol. 14, Issue 3.

E. David Crawford "Use of a Novel Vessel Sealing Technology in Management of the Dorsal Veinous Complex" Sales/Product Literature.

Jarrett et al., "Use of the LigaSure Vessel Sealing System for Peri-Hilar Vessels in Laparoscopic Nephrectomy" Sales/Product Literature.

E. David Crawford "Evaluation of a New Vessel Sealing Device in Urologic Cancer Surgery" Sales/Product Literature.

Joseph Ortenberg "LigaSure System Used in Laparoscopic 1st and 2nd Stage Orchiopexy" Innovations that Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Biopolar Electrothermal Vessel Sealer in Laparoscopically Assisted Vaginal Hysterectomy" Sales/Product Literature.

Johnson et al. "Evaluation of a Bipolar electrothermal Vessel Sealing Device in Hemorrhoidectomy" Sales/Product Literature.

Int'l Search Report PCT/US01/11218, 2001.

Int'l Search Report PCT/US99/24869, 2000.

Int'l Search Report PCT/US98/18640, 1999.

Int'l Search Report PCT/US98/23950, 1999.

PCT/US01/11340, International Search Report, 2001.

PCT/US01/11420, International Search Report, 2001.

PCT/US02/01890, International Search Report, 2002.

PCT/US02/11100, International Search Report, 2002.

PCT/US04/03436, International Search Report, 2005.

PCT/US04/13273, International Search Report, 2004.

PCT/US04/15311, International Search Report, 2005.

EP 98944778, International Search Report, 2000.

EP 98958575, International Search Report, 2002.

EP 04027479, International Search Report, 2005.

EP 04027705, International Search Report, 2005.

EP 04027314, International Search Report, 2005.

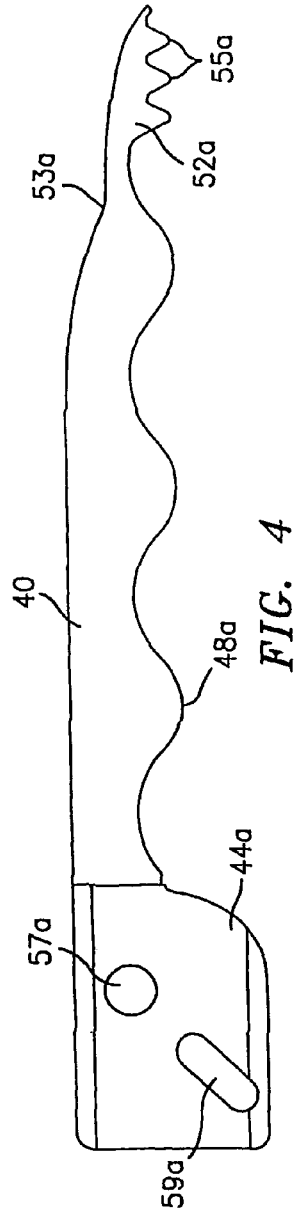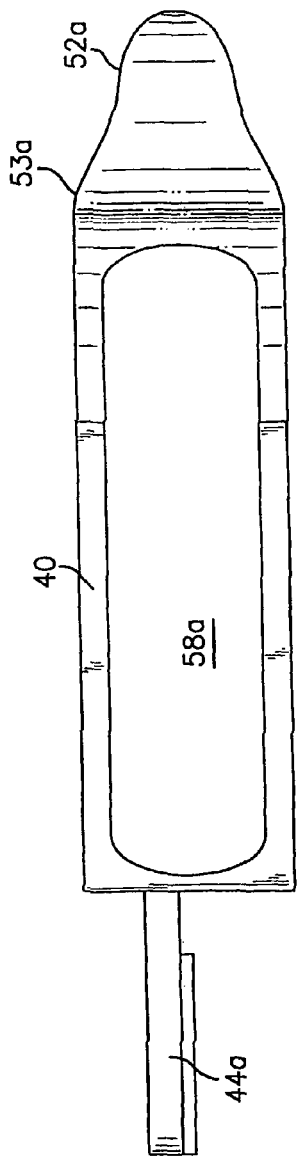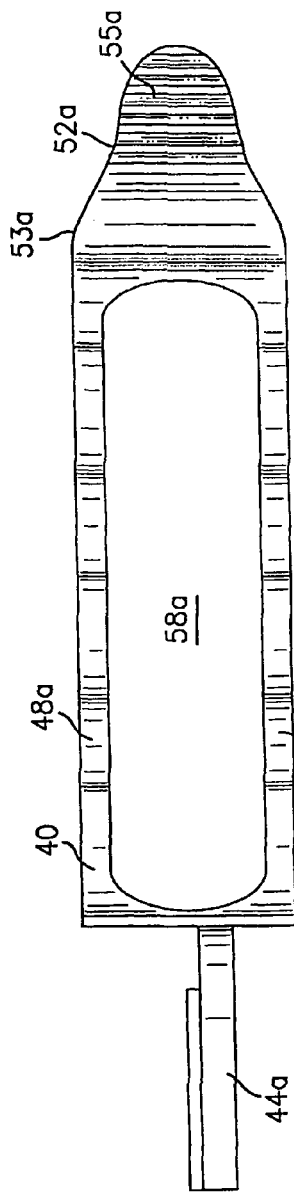

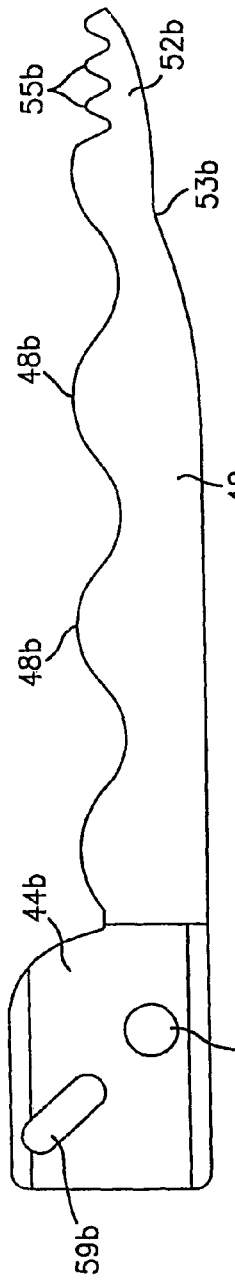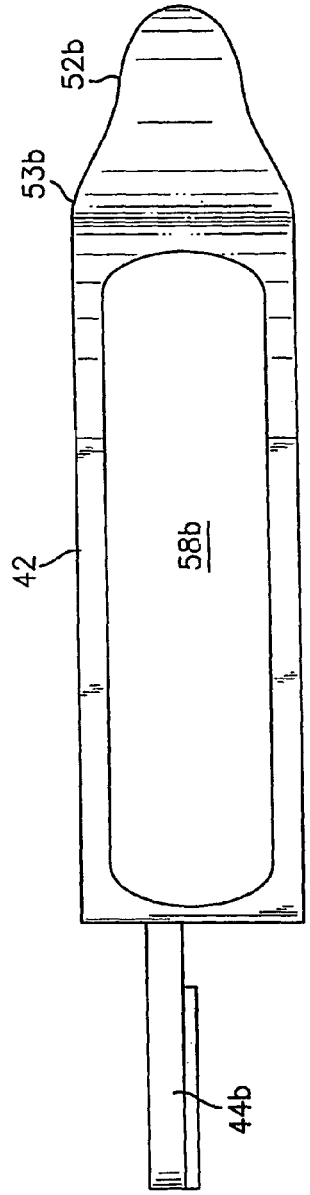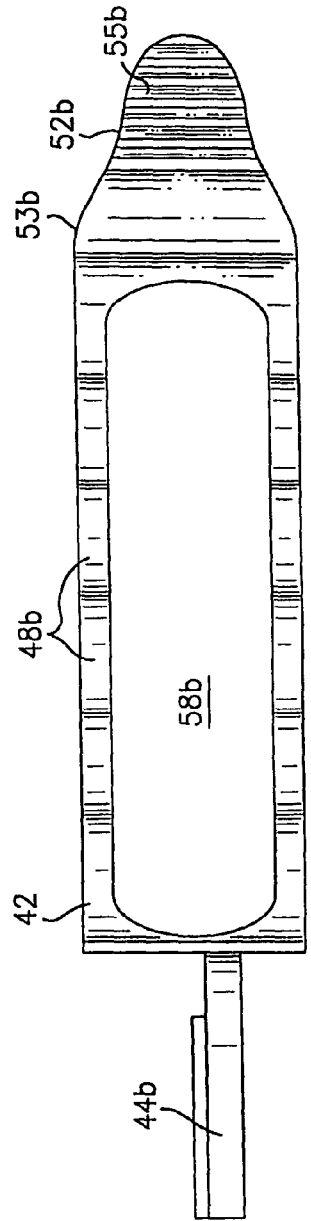

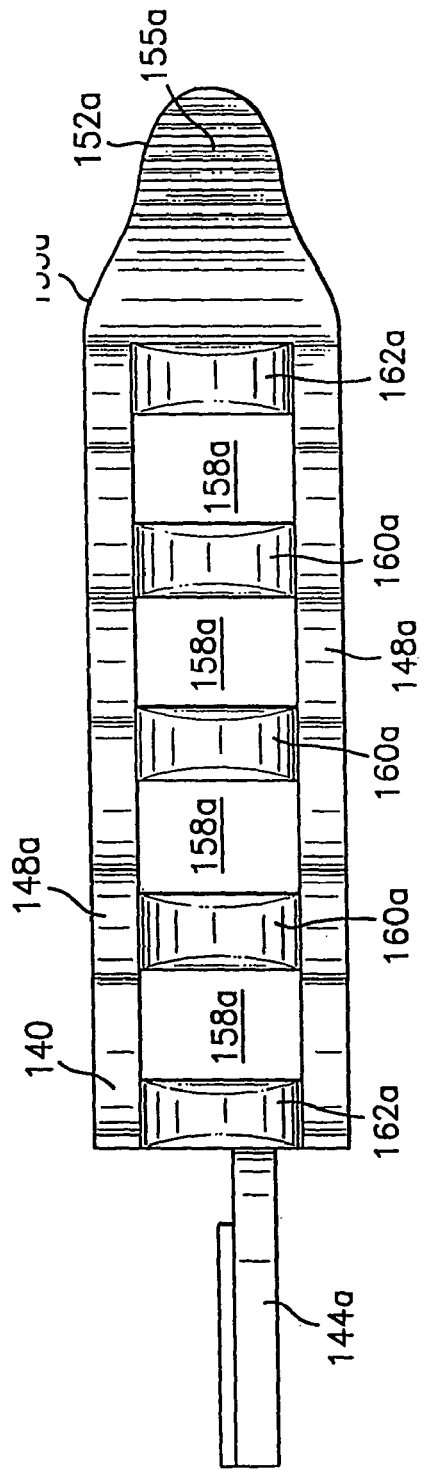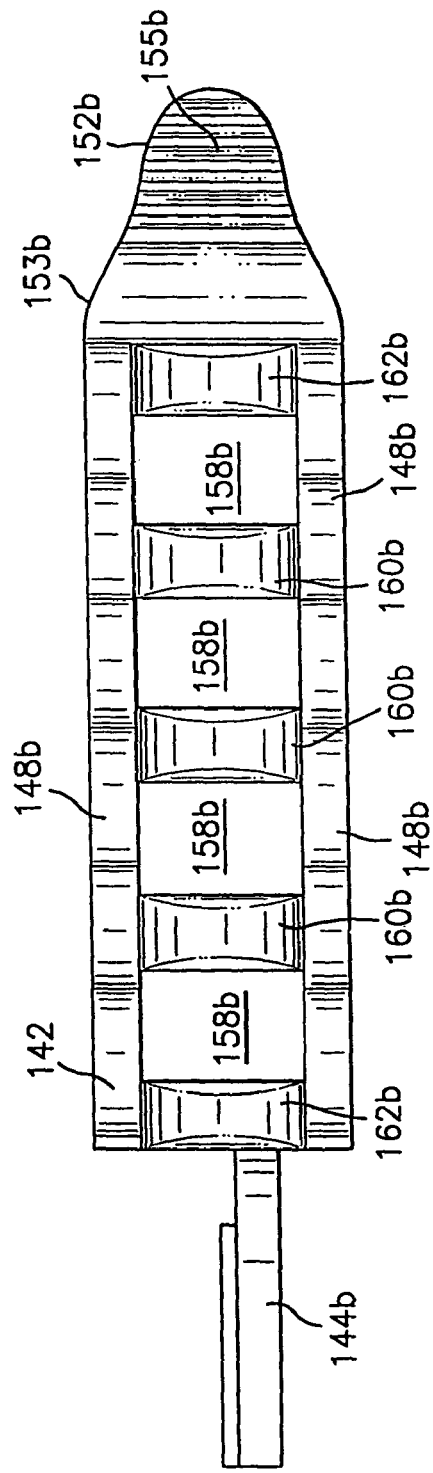

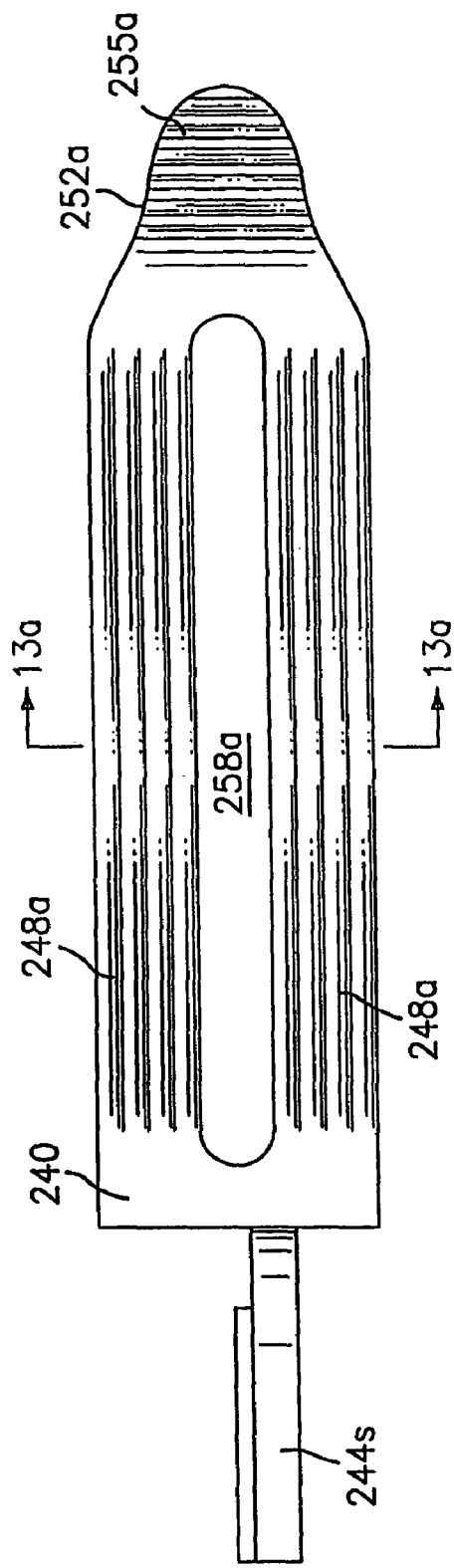
FIG. 12
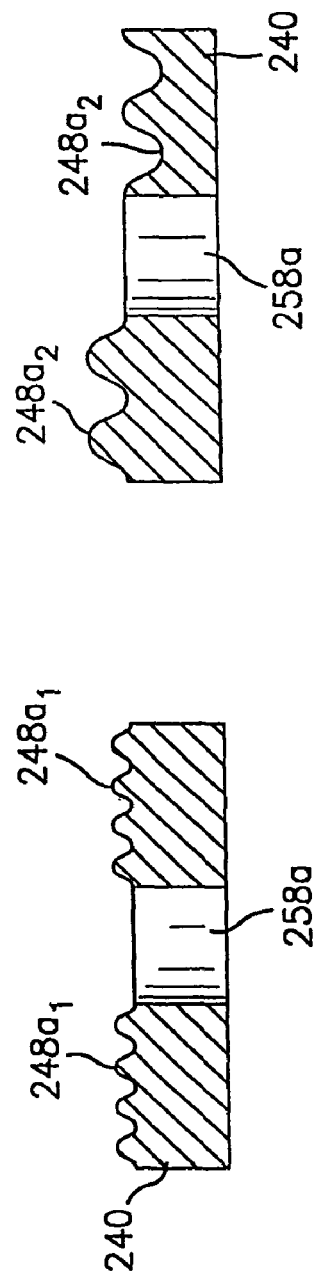
FIG. 13a
FIG. 13b

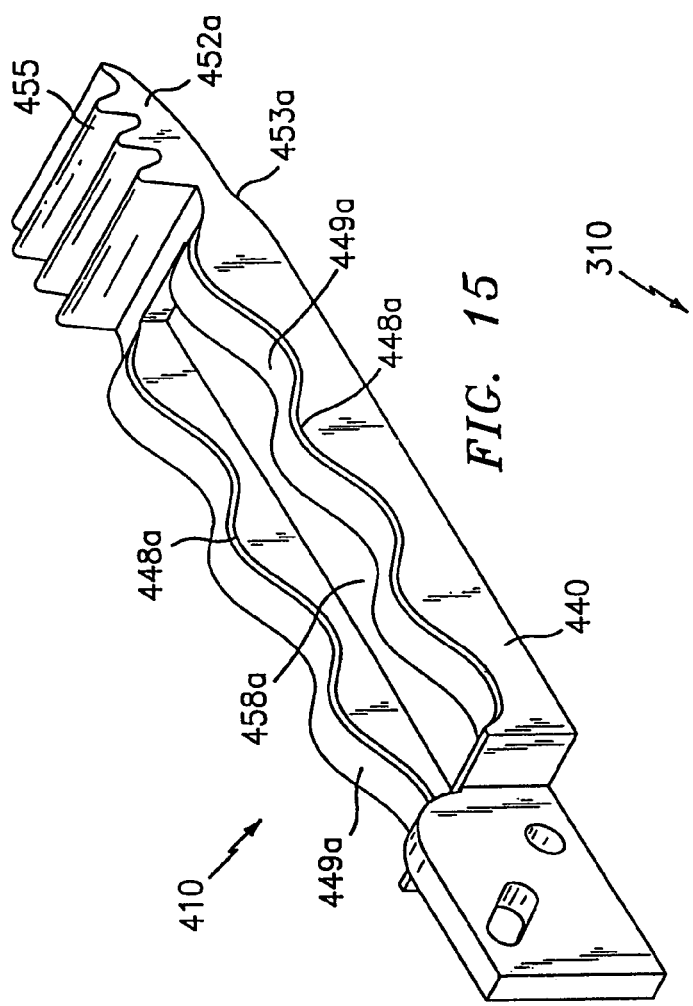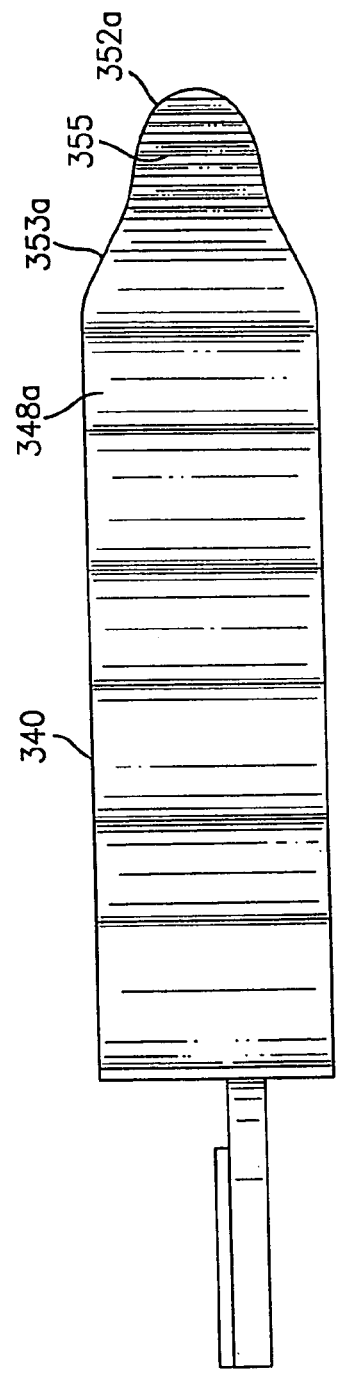

VESSEL SEALING WAVE JAW

CROSS-REFERENCE TO RELATED APPLICATIONS

This application is a continuation of U.S. patent application Ser. No. 09/419,592, filed Oct. 18, 1999, now U.S. Pat. No. 6,887,240, the contents of which is incorporated herein by reference in its entirety.

The present disclosure relates to hemostats or forceps used for open surgical procedures and laparoscopic surgical procedures. More particularly, the present disclosure relates to a fenestrated forceps having wave-like opposing jaws which can be used to apply purely mechanical clamping pressure to clamp, grasp and/or manipulate vascular tissue in an atraumatic fashion or to apply a combination of mechanical clamping pressure and electrosurgical current to cauterize, coagulate/desiccate and/or cut tissue.

TECHNICAL FIELD

A hemostat or forceps is a simple plier-like tool which uses mechanical action between its jaws to constrict vessels and is commonly used in open surgical procedures to grasp, dissect and/or clamp tissue. Electrosurgical forceps are similar clamping devices which utilize both mechanical clamping action and electrical energy to effect hemostasis by heating the tissue and blood vessels to cause coagulation and/or cauterization.

Over the last several decades, more and more surgeons are abandoning traditional open methods of gaining access to vital organs and body cavities in favor of endoscopes and laparoscopic instruments which access organs through small puncture-like incisions. However, due to space limitations surgeons can have difficulty suturing vessels or performing other traditional methods of controlling bleeding, e.g., clamping and/or tying-off transected blood vessels. Electrosurgical instruments and particularly electrosurgical forceps can be used instead to control bleeding.

By utilizing an electrosurgical forceps, a surgeon can either cauterize, coagulate/desiccate and/or cut tissue and/or simply reduce or slow bleeding, by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode. See, e.g., U.S. Pat. Nos. 4,416,276 and 4,416,277 the contents of which are incorporated herein by reference.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

Numerous mechanical and electrosurgical forceps designs have been proposed in the past for various open surgical procedures and laparoscopic surgical procedures. Some of these designs may not provide adequate clamping pressure and/or may cause undue trauma to the tissue during manipulation, clamping and/or coagulation. For example, U.S. Pat. No. 2,518,994 to Miller, U.S. Pat. No. 3,404,677 to Springer and U.S. Pat. No. 5,263,967 to Lyons, III et al. all disclose purely mechanical forceps which have serrated edges or teeth on their respective undersurfaces for grasping and clamping tissue. These structures may have a traumatic effect on delicate tissue. Likewise, U.S. Pat. No. 5,674,220 to Fox et al. and U.S. Pat. No. 5,217,460 to Knoepfler both disclose electrosurgical forceps which also utilize teeth to grasp the tissue and, as a result, may also have a similar traumatic effect on delicate tissue.

Thus, a need exists to develop a forceps which can be utilized effectively without causing needless trauma to tubular vessels or delicate tissues. Preferably, the forceps can be used for both mechanical clamping, grasping and dissecting as well as electrosurgical sealing, coagulation/desiccating and/or cutting of tissue.

SUMMARY

The present disclosure relates to a forceps which includes a shaft portion having a proximal end, a distal end and first and second jaw members pivotally attached to the distal end of the shaft by a pivot assembly. Each of the jaw members includes an opposing inner facing surface having a plurality of wave forms disposed thereon which are capable of engaging tissue therebetween. The plurality of wave forms disposed on the inner facing surface of the second jaw member are complimentary to the plurality of wave forms disposed on the inner facing surface of the first jaw member. The forceps also includes a handle portion attached to the proximal end of the shaft. The handle portion includes an activator assembly disposed therein for imparting movement of the first and second jaw members from a first open position wherein the jaw members are disposed in spaced relation relative to one another to a second clamping position wherein the jaw members cooperate to grasp tissue therebetween.

In one embodiment, the inner facing surfaces of each jaw member include a fenestrated portion disposed therethrough. Preferably, the fenestrated portion of the first jaw member is aligned with the fenestrated portion of the second jaw member.

In another embodiment, the wave forms of the first jaw member include clamping portions and manipulating portions and the wave forms of the second jaw member include complimentary clamping and manipulating portions. Preferably, the plurality of wave forms of each jaw member are longitudinally, transversely and/or both longitudinally and transversely disposed on the inner facing surface of each jaw member.

In yet another embodiment, the manipulating portions of the jaw members include a plurality of teeth which are filleted or rounded to reduce trauma to the tissue. Preferably, the clamping portion of each of the jaw members is wide relative to the manipulating portion to facilitate dissection.

The forceps may be bipolar with each of the inner facing surfaces of the jaw members including an electrode which is connected to a source of electrical energy. The wave forms of the first jaw member include coagulating portions and manipulating portions and the wave forms of the second jaw member include complimentary coagulating and manipulating portions. The source of electrical energy imparts different electrical potentials to each of the electrodes such that the electrodes are capable of conducting bipolar energy through the tissue held between the inner facing surfaces of the jaw members. It is also contemplated that a portion of the inner facing surfaces of each jaw member is non-conductive and/or semi-conductive (i.e., only certain portions of the surface are conductive) to control and/or eliminate current densities at specific jaw locations.

BRIEF DESCRIPTION OF THE DRAWINGS

FIG. 4 is an enlarged, side view of the upper jaw member of FIG. 3 showing a plurality of clamping and manipulating wave portions disposed along an inner facing surface thereof;

FIG. 5 is an enlarged, top view of the upper jaw member of FIG. 3 showing a fenestrated portion disposed therethrough;

FIG. 6 is an enlarged, bottom view of the upper jaw member of FIG. 3 showing the undulating wave forms disposed on the inner facing surface of the upper jaw member of FIG. 3;

FIG. 7 is an enlarged, side view of the lower jaw member of FIG. 3 showing a plurality of clamping and manipulating wave portions disposed along an inner facing surface thereof;

FIG. 8 is an enlarged, top view of the lower jaw member of FIG. 3 showing a fenestrated portion disposed therethrough;

FIG. 9 is an enlarged, bottom view of the lower jaw member of FIG. 3 showing the undulating wave forms disposed on the inner facing surface of the lower jaw member which compliment the wave forms of the upper jaw member;

FIG. 10 is an enlarged, bottom view of another embodiment of the present disclosure showing a plurality of wave forms disposed both longitudinally and transversely along the inner facing surface of the upper jaw member;

FIG. 11 is an enlarged, bottom view of the complimentary lower jaw member of FIG. 10;

FIG. 12 is an enlarged, bottom view of another embodiment of the present disclosure showing a plurality of wave forms disposed transversely along the inner facing surface of the upper jaw member;

FIG. 13a is an enlarged, frontal view in cross-section taken along line 13a-13a of FIG. 12;

FIG. 13b is an enlarged, frontal view in cross-section of another embodiment of the present disclosure showing an alternative transverse wave pattern disposed along the inner facing surface of the upper jaw member.

FIG. 14 is an enlarged, bottom view of another embodiment of the present disclosure showing a plurality of wave forms disposed longitudinally along the inner facing surface of the upper jaw member;

FIG. 15 is an enlarged, perspective view of another embodiment of the present disclosure showing the upper jaw member having electrodes disposed on the inner facing surface of the upper jaw member;

DETAILED DESCRIPTION OF THE PREFERRED EMBODIMENTS

Figure 1:
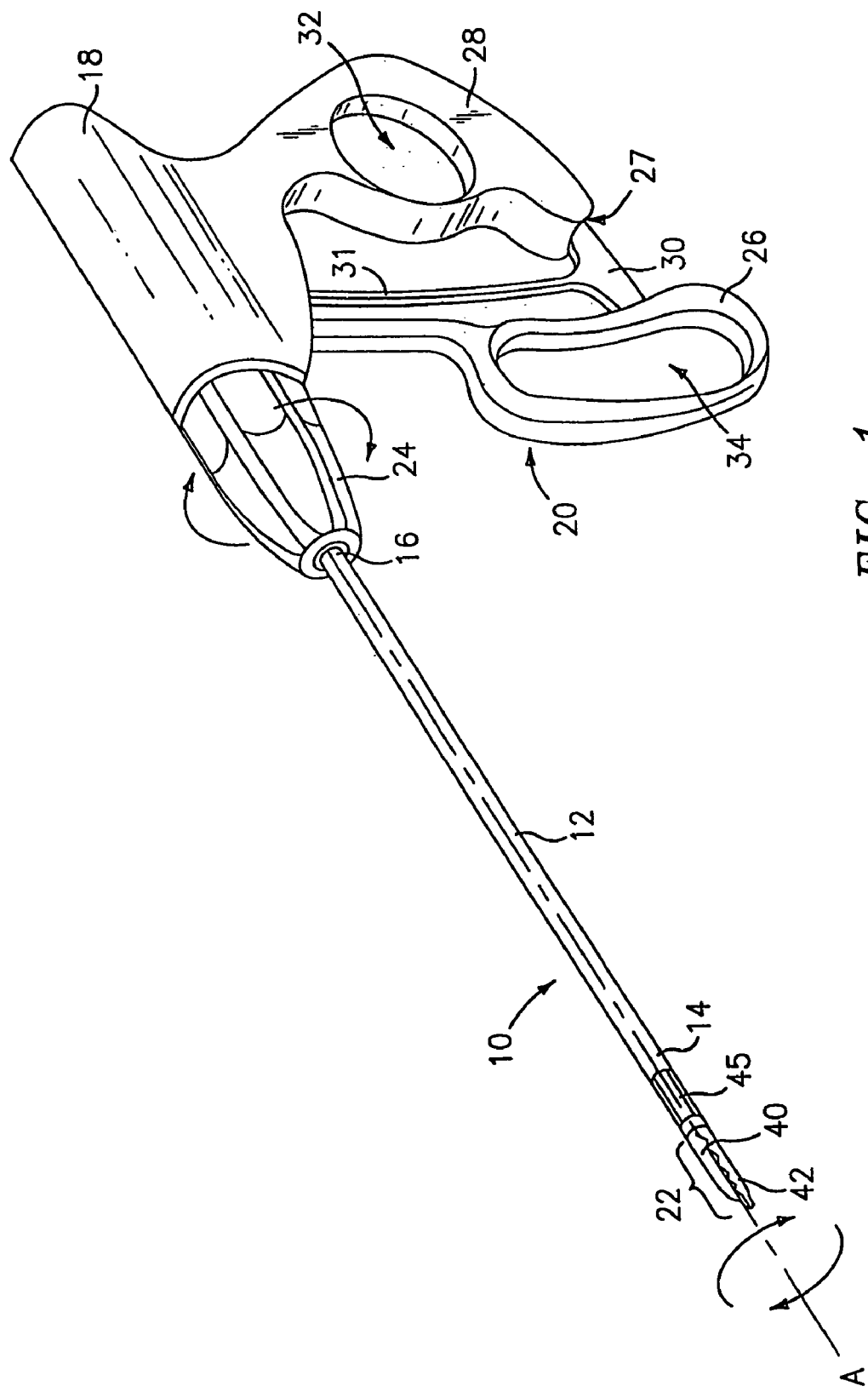
FIG. 1 is a perspective view of a forceps according to the present disclosure.

Referring now to FIG. 1, a forceps 10 for use with open and/or laparoscopic surgical procedures includes an elongated shaft portion 12 having a proximal end 16 and a distal end 14. An end effector assembly 22 is attached to the distal end 14 of shaft 12 and includes a pair of opposing jaw members 40 and 42. Preferably, a handle portion 18 is attached to the proximal end 16 of shaft 12 and includes an activator assembly 20 for imparting movement of the jaw members 40 and 42 from an open position wherein the jaw members 40, 42 are disposed in spaced relation relative to one another, to a clamping or closed position wherein the jaw members 40, 42 cooperate to grasp tissue 51 therebetween.

Activator assembly 20 includes a movable handle 26 having an aperture 34 defined therein for receiving at least one of the operator's fingers and a fixed handle 28 having an aperture 32 defined therein for receiving an operator's thumb. Movable handle 26 is selectively moveable from a first position relative to fixed handle 28 to a second position in closer proximity to the fixed handle 28 to close jaw members 40, 42. Preferably, fixed handle 28 includes a channel 27 which extends proximally for receiving a ratchet 30 which is coupled to movable handle 26. This structure allows for progressive closure of end effector assembly 22 as well as locking engagement of opposing jaw members 40, 42.

In some cases it may be preferable to include other mechanisms to control and/or limit the movement of handle 26 relative to handle 28 such as, e.g., hydraulic, semi-hydraulic and/or gearing systems.

Handle portion 18 may also include a rotation knob 24 for controlling the rotational movement of the end effector assembly 22 about a longitudinal axis "A" of the elongated shaft 12. Preferably, the ratio of rotation of the knob 24 to the end effector assembly 22 is 1:1, however, it is contemplated that gearing structure may be incorporated to increase or decrease the rotational ratio depending upon a particular purpose.

Figure 2:
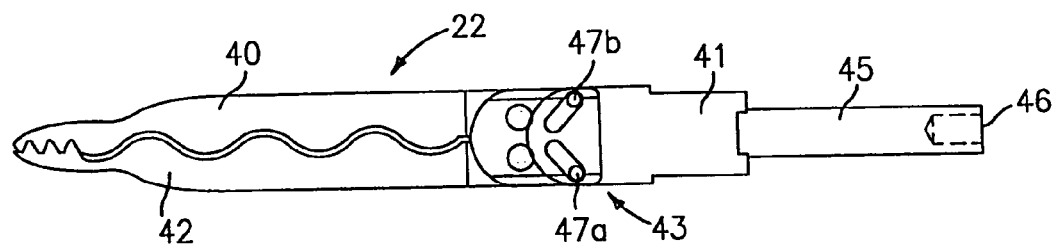
FIG. 2 is an enlarged, side view of a pair of jaw members of the forceps of FIG. 1 shown in closed configuration.
Figure 3:
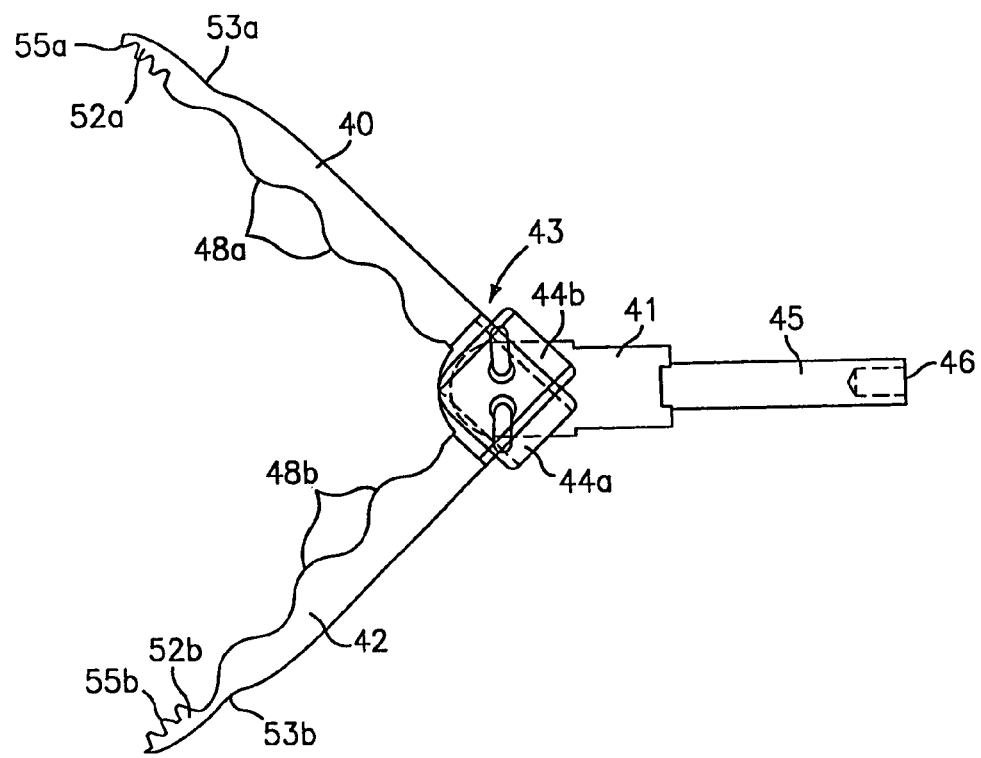
FIG. 3 is an enlarged, side view of a pair of jaw members of the forceps of FIG. 1 shown in open configuration.

FIGS. 2 and 3 show enlarged views of the end effector 22 which includes a first or upper jaw member 40 and a second or lower jaw member 42 which are disposed in opposing relation about pivot assembly 43. End effector 22 also includes a pivot housing 41 and a rod 45 having a coupler 46 which matingly engages the distal end 14 of shaft 12. The pivot assembly 43 includes a first pivot portion 44a attached to the upper jaw member 40 and a second pivot portion 44b attached to the lower jaw member 42 which are each affixed to the pivot housing 41 by pins 47a and 47b, respectively. As explained in detail above, movement of handle 26 effects movement of the jaw members 40, 42 about the pin assembly 43 from an open position (FIG. 3) to a closed position (FIG. 2).

Each jaw member 40, 42 includes a plurality of wave forms disposed along its inner facing surface which cooperate to engage tissue 51 therebetween. Preferably, each jaw member 40 and 42 includes clamping wave portions 48a and 48b and manipulating wave portions 52a and 52b, respectively (FIG. 3). The clamping and manipulating wave portions 48b, 58b, respectively, disposed on the inner facing surface of the lower jaw member 42 are complimentary (out of phase) to the clamping and manipulating wave portions 48a, 58a, respectively, of the upper jaw member 40 thus, the upper and lower jaws interfit in the closed position (FIG. 2).

In one embodiment of the present disclosure, the clamping wave portions 48a, 48b are disposed along a proximal portion of each jaw member's 40, 42 length and the manipulating wave portions 52a, 52b are tapered at or about step 53a, 53b to facilitate dissection. In some cases, however, it may be preferable to adjust the length of the clamping wave portions 48a, 48b relative to the manipulating wave portions 53a, 53b to suit a particular purpose. Preferably, the radius of curvature of the clamping wave portions 48a, 48b is greater than the radius of curvature of the manipulating wave portions 52a, 52b. More particularly, the manipulating wave portions 52a, 52b preferably include a plurality of small peaks 55a and 55b which facilitate dissection and delicate positioning of tissue. The clamping wave portions 48a, 48b, on the other hand, preferably include larger, more undulating, wave patterns to improve atraumatic grasping of large structures and to increase surface area contact. In another embodiment of the present disclosure, the small peaks 55a, 55b are filleted to reduce trauma to the tissue 51. It is also envisioned that by filleting peaks 55a, 55b and the areas between successive peaks 55a, 55b, areas of high current densities which typically occur at or along sharp edges/points and which may cause tissue damage, e.g., tissue sticking and charring, will be reduced.

FIGS. 4-9 show enlarged views of the jaw members 40, 42 of the present disclosure. More particularly, FIGS. 4-6 show upper jaw member 40 which includes clamping wave portions 48a and manipulating wave portions 52a which extend in a longitudinal fashion along the inner facing surface of jaw member 40. Likewise, FIGS. 7-9 show lower jaw member 42 which includes complimentary clamping wave portions 48b and manipulating wave portions 52b which also extend in a longitudinal fashion along the inner facing surface jaw member 42.

Jaw members 40, 42 also include apertures 57a and 57b, respectively, and slots or cams 59a and 59b which are each disposed within respective pivot portions 44a and 44b and mount jaw members 40, 42 about pivot pins 47a and 47b, respectively to pivot housing 41 (see FIGS. 2 and 3). Preferably, slots 59a, 59b effect opposing linear movement of the jaw members 40, 42 about pins 47a, 47b. However, in some cases it may be preferable to manufacture slots or cams 59a, 59b with a different shape, e.g., harmonic, parabolic and/or cycloidal, to move the jaw members 40, 42 in a different and/or more prescribed manner.

As seen best in FIGS. 5, 6, 8 and 9 each jaw member 40, 42 also includes an elongated fenestration 58a, 58b disposed therethrough which is preferably dimensioned about the same length as the clamping wave portion 48a, 48b of each jaw member 40, 42. It is envisioned that when tissue 51 is grasped between clamping wave portions 48a, 48b, the fenestration feature of the jaw members 40, 42 will cause the tissue 51 to inundate fenestrations 58a, 58b thus providing better atraumatic holding/grasping of the tissue 51.

FIGS. 6 and 9 illustrate one possible wave pattern for the opposing inner facing surfaces of the upper jaw member 40 and the lower jaw member 42, respectively. It is envisioned that any plurality of wave patterns can be utilized depending upon a particular purpose. For example, with this embodiment, the wave pattern includes clamping wave portions 48a, 48b which run longitudinally along either side of fenestration 58a, 58b and manipulating wave portions which also run longitudinally from step 53a, 53b to the distal end of each jaw member 40, 42. It is envisioned that providing wave patterns on the clamping wave portion 48a, 48b of the inner facing surfaces of the jaw members 40, 42 will require more of the tissue 51 to circumnavigate these waves/curves thus providing better grasping power of the tissue 51. In addition, the fenestration feature will also require the tissue 51 to inundate the fenestrations 58a, 58b causing the tissue 51 to hold on an additional or second plane.

FIGS. 10-13b show other wave patterns which can be formed on the inner facing surfaces of the jaw members 40, 42. For example, FIGS. 10 and 11 show a plurality of fenestrations 158a disposed along the inner facing surfaces of each jaw member 40, 42 and the wave pattern includes both longitudinally disposed clamping wave portions 148a, 148b and transversely disposed wave portions 160a, 162a and 160b, 162b. More particularly, the clamping wave portions 148a, 148b run longitudinally along either side of the plurality of fenestrations 158a, 158b and the manipulating wave portions 152a, 152b run longitudinally from step 153a, 153b to the distal end of each jaw member 140, 142. Wave patterns 160a, 160b run transversely between fenestrations 158a, 158b and wave patterns 162a, 162b run transversely at either end of the plurality of fenestrations 158a, 158b.

FIGS. 12, 13a and 13b show yet other possible wave patterns which can be employed along the inner facing surfaces of the jaw members. For illustrative purposes, the upper jaw member 240 is shown but it is envisioned that the lower jaw member of this embodiment is simply complimentary to the upper jaw member 240. FIGS. 12 and 13a show clamping wave portions $248a_1$ having a transverse wave pattern (a wave pattern which extends axially across upper jaw member 240) disposed on either side of fenestration 258a. FIG. 13b shows another possible transverse wave pattern for the clamping wave portions $248a_2$ along the inner facing surface of the upper jaw member 240. It is envisioned that all of the these wave patterns and accompanying fenestrations will provide better atraumatic grasping of the tissue 51 along the various planes and some wave patterns may be better suited for particular purposes.

FIG. 14 shows a forceps 310 having yet another wave pattern employed along the inner facing surfaces of the jaw members. Clamping wave portion 348a includes a longitudinal wave pattern generally disposed across the inner facing surface of the jaw member 340 and manipulating wave portion 352a extending from step 353a to the distal end of upper jaw member 340. In this embodiment, the fenestration feature is not included.

Figure 16:
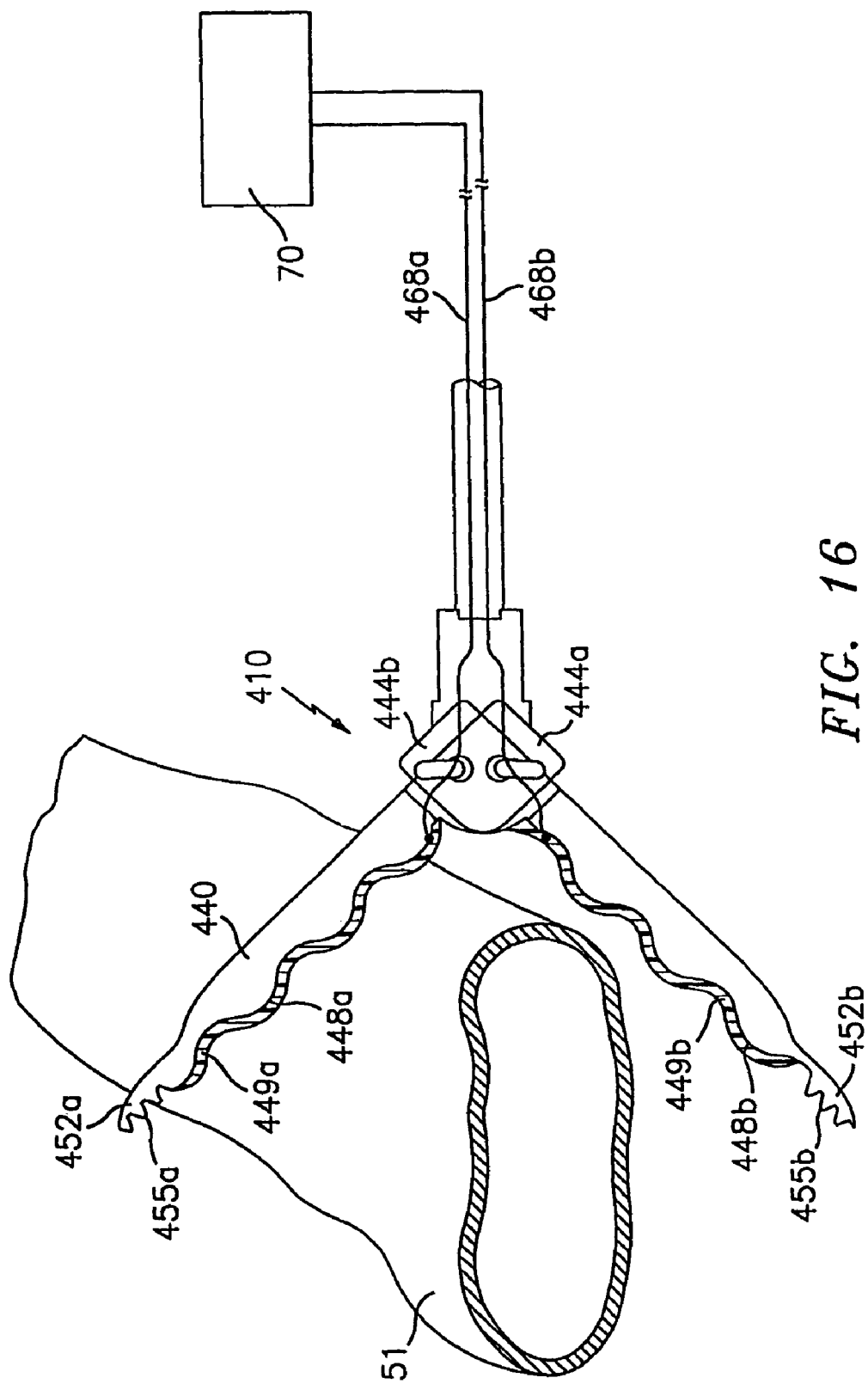
FIG. 16 is a side view showing two jaw members in open configuration prior to engagement about a tubular vessel.
Figure 17:
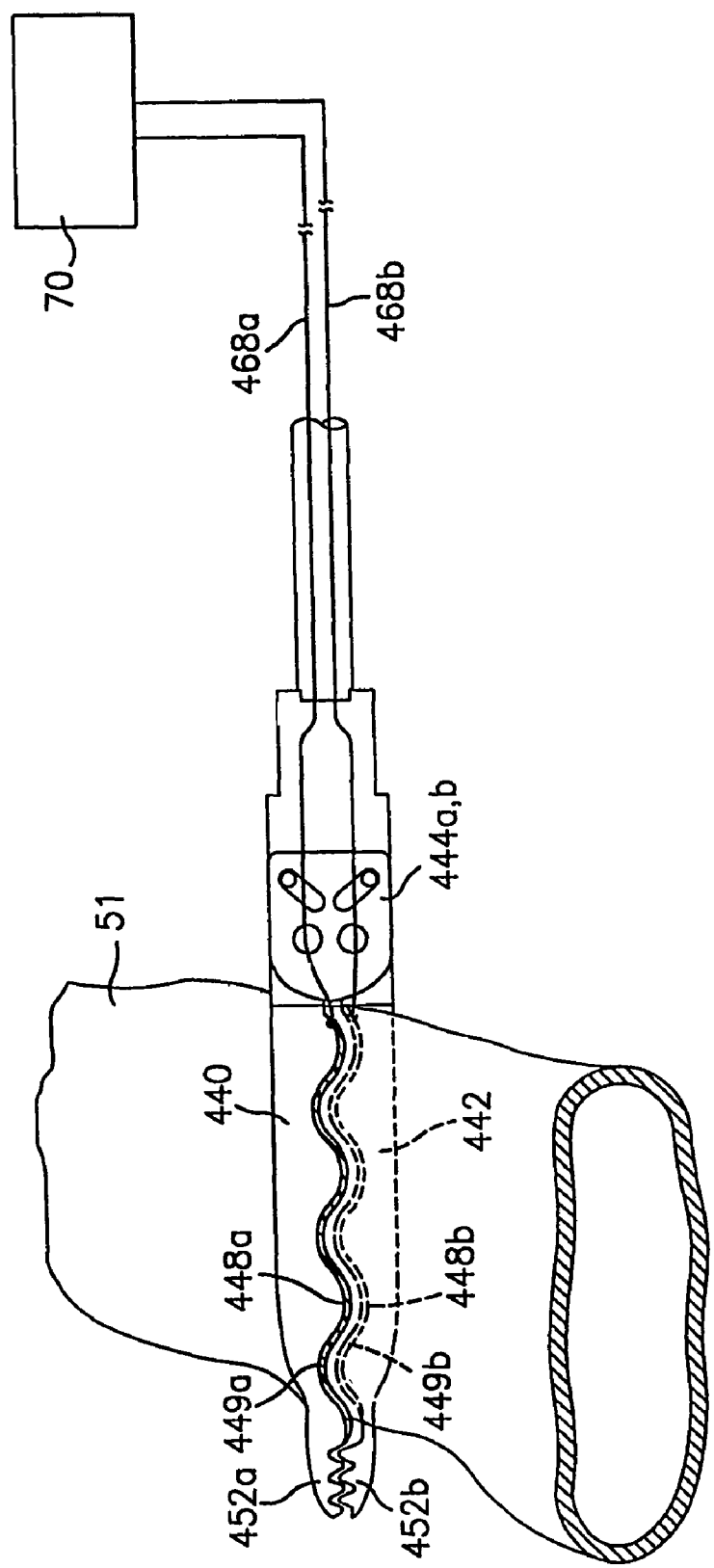
FIG. 17 is a side view showing the two jaw members of FIG. 16 in closed configuration about a tubular vessel.

FIGS. 15-17 illustrate a bipolar forceps 410 according to the present disclosure which includes a plurality of coagulating wave portions 448a, 448b and a plurality of manipulating wave portions 452a, 452b disposed along the inner facing surface of each jaw member 440, 442. Preferably, the forceps also includes at least one electrode 449a, 449b disposed on the inner facing surface of each jaw member 440, 442 and at least one fenestration 458a, 458b disposed through each jaw member 440, 442. As mentioned above with the other embodiments of the present disclosure, it is envisioned that the fenestration feature of the jaw members 440, 442 causes the tissue 51 to inundate fenestrations 458a, 458b providing better atraumatic holding/grasping of the tissue. It is envisioned that one or perhaps several of the aforedescribed wave patterns may also be used to improve vessel sealing and/or coagulation with this particular embodiment of the present disclosure.

For the purposes herein the term coagulation is defined as a process of desiccating tissue wherein the tissue cells are ruptured and dried. Vessel sealing is defined as the process of liquefying the collagen in the tissue so that it crosslinks and reforms into a fused mass.

As best seen in FIGS. 16 and 17, each electrode 449a, 449b is electrically coupled to an electrosurgical generator 70 by a cable 468a, 468b, respectively. The generator 70 imparts different electrical potentials to each electrode 449a, 449b and since tissue 51 is a conductor of electrical energy, when the upper and lower jaw members, 440, 442, respectively, grasp tissue 51 therebetween, the electrical energy is transferred through the tissue 51. By controlling the intensity, frequency and duration of the electrosurgical energy applied to the tissue 51, and, to a certain extent, by controlling the mechanical clamping pressure applied to the tissue 51, the surgeon can either cauterize, coagulate/desiccate and/or cut tissue and/or simply reduce or slow bleeding.

The electrodes 449a, 449b are disposed along the coagulating wave portions 448a, 448b of the jaw members 440, 442 and are generally shaped according to the contours and undulating patterns of the coagulating wave portions 448a, 448b. Preferably, portions of the inner facing surfaces of each jaw member 440, 442 are non-conductive and/or semi-conductive to control or eliminate undesirable current densities which may convene at these locations. For example, an insulative coating could be applied to the small peaks 455a, 455b to reduce the possibility of electrical shorting when the forceps 410 is sealing/coagulating tissue 51 grasped in the coagulating wave portions 448a, 448b of the jaw members 440, 442. Moreover, various metal alloys could be employed to add non-stick characteristics to the bipolar forceps 410.

In addition to rendering the forceps 410 atraumatic and improving its overall grasping features by the provision of fenestrations and various wave patterns disposed along the inner facing surfaces of the jaw members 440, 442, the wave features of the forceps 410 increase the overall surface area for welding vessels and other anatomical structures which is believed to provide superior tissue sealing effects.

In use, the surgeon manipulates handle 26 to advance the activator assembly 20 and move jaw members 440, 442 to the open position wherein the jaw members 440, 442 are disposed in spaced relation relative to one another to receive tissue 51 therebetween. The surgeon then manipulates handle 26 to impart movement of the jaw members 440, 442 about pivot portions 444a, 444b to close the inner facing surfaces of the jaw members 440, 442 about tissue 51.

Depending upon the surgeons particular purpose, the surgeon can close either the coagulating wave portions 448a, 448b and/or the manipulating wave portions 452a, 452b about the tissue 51 to coagulate/seal/cut and/or delicately manipulate the tissue 51. If the surgeon's purpose is to coagulate/seal/cut the tissue 51, then after the jaw members 440, 442 are closed about the tissue 51, the surgeon then applies electrosurgical energy to the tissue 51. By controlling the intensity, frequency and duration of the electrosurgical energy applied to the tissue 51, the surgeon can either cauterize, coagulate/desiccate and/or cut tissue and/or simply reduce or slow bleeding.

From the foregoing and with reference to the various figure drawings, those skilled in the art will appreciate that certain modifications can also be made to the present disclosure without departing from the scope of the present disclosure. For example, it is envisioned that various longitudinal, transverse wave patterns can be formed on the jaw members depending upon a particular purpose. In addition, the shape and size of the fenestrations may also be altered to meet a particular purpose.

Although it is preferable to form the upper and lower jaw members such that they are complimentary and intermesh with one another, in some cases it may be preferable to include non-complimentary portions depending upon a particular purpose. Moreover, it may be preferable to offset the upper jaw member fenestrations from the lower jaw member fenestrations.

Although it is preferable to vertically align the electrodes on the bipolar version of the forceps, in some cases it may be preferable to offset the opposing electrodes relative to one another either longitudinally or transversely to suit a particular purpose.

In addition, it may be preferable to add other features to the forceps of the present disclosure, e.g., an articulating assembly to axially displace the end effector assembly relative to the elongated shaft.

There have been described and illustrated herein several embodiments of a forceps having wave-like opposing jaws for clamping, grasping, manipulating, cauterizing, coagulating/desiccating and/or cutting vascular tissue in an atraumatic fashion. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. In a forceps having first and second jaw members operatively attached adjacent a distal end thereof and a handle assembly adjacent a proximal end thereof, the jaw members being movable between an open position and a closed position about a pivot assembly, the improvement comprising opposing inner facing surfaces disposed distal to the pivot assembly each having a plurality of different waveforms disposed thereon, the inner facing surface of at least one of the jaw members having at least one fenestration disposed therethrough between the plurality of waveforms.

2. A forceps according to claim 1 wherein the plurality of waveforms of the first jaw member comprises clamping portions and manipulating portions and the plurality of waveforms of the second jaw member comprises complimentary clamping and manipulating portions.

3. A forceps according to claim 2 wherein the clamping portion of each of the jaw members is wider than the manipulating portion of each of the jaw members.

4. A forceps according to claim 2 wherein the manipulating portions of each of the jaw members are filleted to reduce trauma to the tissue.

5. A forceps according to claim 1 wherein the plurality of waveforms of each of the first and the second jaw members are longitudinally disposed on the inner facing surface of each jaw member.

6. A forceps according to claim 1 wherein the plurality of wave forms of each of the first and the second jaw members are transversely disposed on the inner facing surface of each jaw member.

7. A forceps according to claim 1 wherein the first and second jaw members comprise a first plurality of wave forms longitudinally disposed on the inner facing surface of each of the jaw members and a second plurality of wave forms transversely disposed on the inner facing surface of each of the jaw members.

8. A forceps according to claim 1 wherein at least one portion of the inner facing surface of each of the jaw members is coated with a non-stick coating.

9. A forceps according to claim 1 wherein at least one portion of each of the inner facing surfaces of each of the jaw members is non-conductive.

10. A forceps according to claim 1 wherein at least one portion of each of the inner facing surfaces of each of the jaw members is semi-conductive.

11. A forceps, comprising:
a shaft portion having a proximal end and a distal end;
first and second jaw members pivotally attached to the distal end of the shaft by a pivot assembly, each of the jaw members comprising an opposing inner facing surface disposed distal of the pivot assembly and having a plurality of waveforms disposed thereon, the opposing inner facing surfaces capable of engaging tissue therebetween;

the plurality of waveforms disposed on the inner facing surface of the second jaw member being complimentary to the plurality of wave forms disposed on the inner facing surface of the first jaw member;

the inner facing surface of at least one of the jaw members having at least one fenestrated portion disposed therethrough between the plurality of waveforms; and a handle portion attached to the proximal end of the shaft, the handle portion having an activator assembly disposed therein for imparting movement of the first and second jaw members from a first open position wherein the jaw members are disposed in spaced relation relative to one another to a second clamping position wherein the jaw members cooperate to grasp tissue therebetween.

12. A forceps according to claim 11 wherein the inner facing surfaces of both of the jaw members have at least one fenestrated portion disposed therethrough between the plurality of waveforms.

13. A forceps according to claim 12 wherein at least one of the fenestrated portions of the inner facing surface of the first jaw member is vertically aligned with at least one of the fenestrated portions of the inner facing surface of the second jaw member.

14. A forceps according to claim 11 wherein the plurality of waveforms of the first jaw member comprises clamping portions and manipulating portions and the plurality of waveforms of the second jaw member comprises complimentary clamping and manipulating portions.

15. A forceps according to claim 14 wherein the manipulating portions of each of the jaw members are filleted to reduce trauma to the tissue.

16. A forceps according to claim 11 wherein the plurality of waveforms of each of the first and the second jaw members are longitudinally disposed on the inner facing surface of each jaw member.

17. A forceps according to claim 11 wherein the plurality of wave forms of each of the first and the second jaw members are transversely disposed on the inner facing surface of each jaw member.

18. A forceps according to claim 11 wherein the forceps comprises a first plurality of wave forms longitudinally disposed on the inner facing surface of each of the jaw members and a second plurality of wave forms transversely disposed on the inner facing surface of the jaw member.

19. A forceps according to claim 11 wherein at least one portion of the inner facing surface of each of the jaw members is coated with a non-stick coating.

20. A forceps according to claim 11 wherein at least one portion of each of the inner facing surfaces of each of the jaw members is nonconductive.

21. A forceps according to claim 11 wherein at least one portion of each of the inner facing surfaces of each of the jaw members is semi-conductive.

22. In a forceps having first and second jaw members operatively attached adjacent a distal end thereof and a handle assembly adjacent a proximal end thereof, the jaw members being movable between an open position and a closed position about a pivot assembly, the improvement comprising opposing inner facing surfaces disposed distal to the pivot assembly each having a plurality of different waveforms disposed thereon and at least one electrode disposed thereon, the inner facing surface of at least one of the jaw members having at least one fenestration disposed therethrough between the plurality of waveforms.

23. A bipolar electrosurgical forceps, comprising:

a shaft portion having a proximal end and a distal end;

first and second jaw members pivotally attached to the distal end of the shaft by a pivot assembly, each of the jaw members comprising an opposing inner facing surface disposed distal to the pivot assembly and having a plurality of waveforms and at least one electrode disposed thereon, the opposing inner facing surfaces capable of engaging tissue therebetween;

the plurality of waveforms disposed on the inner facing surface of the second jaw member being complimentary to the plurality of waveforms disposed on the inner facing surface of the first jaw member;

a connector for connecting the electrodes to a source of electrical energy such that the electrodes disposed on the first jaw member have a first electrical potential and the electrodes of the second jaw member have a second electrical potential and the electrodes are capable of conducting bipolar energy through the tissue held between the inner facing surfaces;

the inner facing surface of at least one of the jaw members having at least one fenestrated portion disposed therethrough between the plurality of waveforms; and a handle attached to the proximal end of the shaft, the handle having an activator assembly disposed therein for imparting movement of the first and second jaw members from a first open position wherein the jaw members are disposed in spaced relation relative to one another to a second clamping position wherein the jaw members cooperate to grasp tissue therebetween.

24. A bipolar electrosurgical forceps according to claim 23 wherein at least one of the electrodes of the first jaw member is vertically aligned with at least one electrode of the second jaw member.

25. A bipolar electrosurgical forceps according to claim 23 wherein the plurality of waveforms of the first jaw member comprises coagulating portions and manipulating portions and the plurality of waveforms of the second jaw member comprises complimentary coagulating and manipulating portions.

26. A bipolar electrosurgical forceps according to claim 25 wherein the manipulating portions of each of the jaw members are filleted to reduce trauma to the tissue.

27. A forceps according to claim 25 wherein the coagulation portion of each of the jaw members is wide relative to the manipulating portion of each of the jaw members.

28. A forceps according to claim 25 wherein at least one portion of each of the manipulating portion of each the jaw member is non-conductive.

29. A forceps according to claim 23 wherein at least one portion of each of the inner facing surfaces of each of the jaw members is non-conductive.

30. A forceps according to claim 23 wherein at least one portion of each of the inner facing surfaces of each of the jaw members is semi-conductive.

* * * * *